United States Patent
Cai et al.

(10) Patent No.: US 9,040,929 B2
(45) Date of Patent: *May 26, 2015

(54) CHARGE SENSORS USING INVERTED LATERAL BIPOLAR JUNCTION TRANSISTORS

(75) Inventors: Jin Cai, Cortlandt Manor, NY (US); Tak H. Ning, Yorktown Heights, NY (US); Jeng-Bang Yau, Yorktown Heights, NY (US); Sufi Zafar, Briarcliff Manor, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/561,671

(22) Filed: Jul. 30, 2012

(65) Prior Publication Data
US 2014/0027871 A1    Jan. 30, 2014

(51) Int. Cl.
*G01T 1/24* (2006.01)
*H01L 31/115* (2006.01)
*H01L 27/146* (2006.01)

(52) U.S. Cl.
CPC ......... *H01L 31/115* (2013.01); *H01L 27/14681* (2013.01)

(58) Field of Classification Search
CPC .......................... H01L 27/14; H01L 27/14681
USPC .............................................. 250/267; 438/56
See application file for complete search history.

(56) References Cited

U.S. PATENT DOCUMENTS

| | | | |
|---|---|---|---|
| 3,952,325 A * | 4/1976 | Beale et al. | 365/185.1 |
| 4,469,945 A * | 9/1984 | Hoeberechts et al. | 250/370.01 |
| 4,901,121 A * | 2/1990 | Gibson et al. | 257/29 |
| 4,994,406 A | 2/1991 | Vasquez et al. | |
| 5,309,085 A | 5/1994 | Sohn | |
| 5,332,903 A | 7/1994 | Buehler et al. | |
| 5,486,481 A | 1/1996 | Sundaram | |
| 5,580,553 A | 12/1996 | Nakajima | |
| 5,654,662 A * | 8/1997 | Prentice | 327/478 |
| 5,753,920 A | 5/1998 | Buehler et al. | |
| 5,929,448 A | 7/1999 | Zimmerman | |
| 5,994,739 A | 11/1999 | Nakagawa et al. | |
| 6,512,663 B1 * | 1/2003 | Okushima | 361/111 |
| 6,717,154 B2 | 4/2004 | Black et al. | |

(Continued)

FOREIGN PATENT DOCUMENTS

| JP | 60158372 A | 8/1985 |
|---|---|---|
| JP | 1240885 A | 9/1989 |

OTHER PUBLICATIONS

Cai, J., et al. "Complementary Thin-Base Symmetric Lateral Bipolar Transistors on SOI" 2011 IEEE. pp. 386-389.

(Continued)

*Primary Examiner* — Kiho Kim
(74) *Attorney, Agent, or Firm* — Tutunjian & Bitetto, P.C.; Louis J. Percello

(57) ABSTRACT

A sensor includes a collector, an emitter and a base-region barrier formed as an inverted bipolar junction transistor having a base substrate forming a base electrode to activate the inverted bipolar junction transistor. A level surface is formed by the collector, the emitter and the base-region barrier opposite the base substrate such that when the level surface is exposed to charge, the charge is measured during operation of the bipolar junction transistor.

17 Claims, 9 Drawing Sheets

(56) References Cited

U.S. PATENT DOCUMENTS

| | | |
|---|---|---|
| 6,995,376 B2 | 2/2006 | Cottrell et al. |
| 7,038,249 B2 | 5/2006 | Suligoj et al. |
| 7,816,653 B2 | 10/2010 | Aurola |
| 8,053,740 B2 | 11/2011 | Stahmann et al. |
| 2002/0130335 A1* | 9/2002 | Inbe .............................. 257/225 |
| 2011/0241152 A1* | 10/2011 | Hsiao et al. .................. 257/447 |
| 2012/0068225 A1* | 3/2012 | Gravrand et al. ............. 257/184 |
| 2012/0139009 A1 | 6/2012 | Ning et al. |
| 2013/0119516 A1* | 5/2013 | Harame et al. ................ 257/565 |

OTHER PUBLICATIONS

Li, Y., et al. "Probing Proton Damage in SOI CMOS Technology by Using Lateral Bipolar Action" IEEE Transactions on Nuclear Science, vol. 50, No. 6. Dec. 2003. pp. 1885-1890.

Ratti, L., et al. "Response of SOI Bipolar Transistors Exposed to Y-Rays Under Different Dose Rate and Bias Conditions" IEEE Transactions on Nuclear Science, vol. 52, No. 4. Aug. 2005. pp. 1040-1047.

Office Action dated Jun. 6, 2004 for U.S. Appl. No. 13/566,324.

* cited by examiner

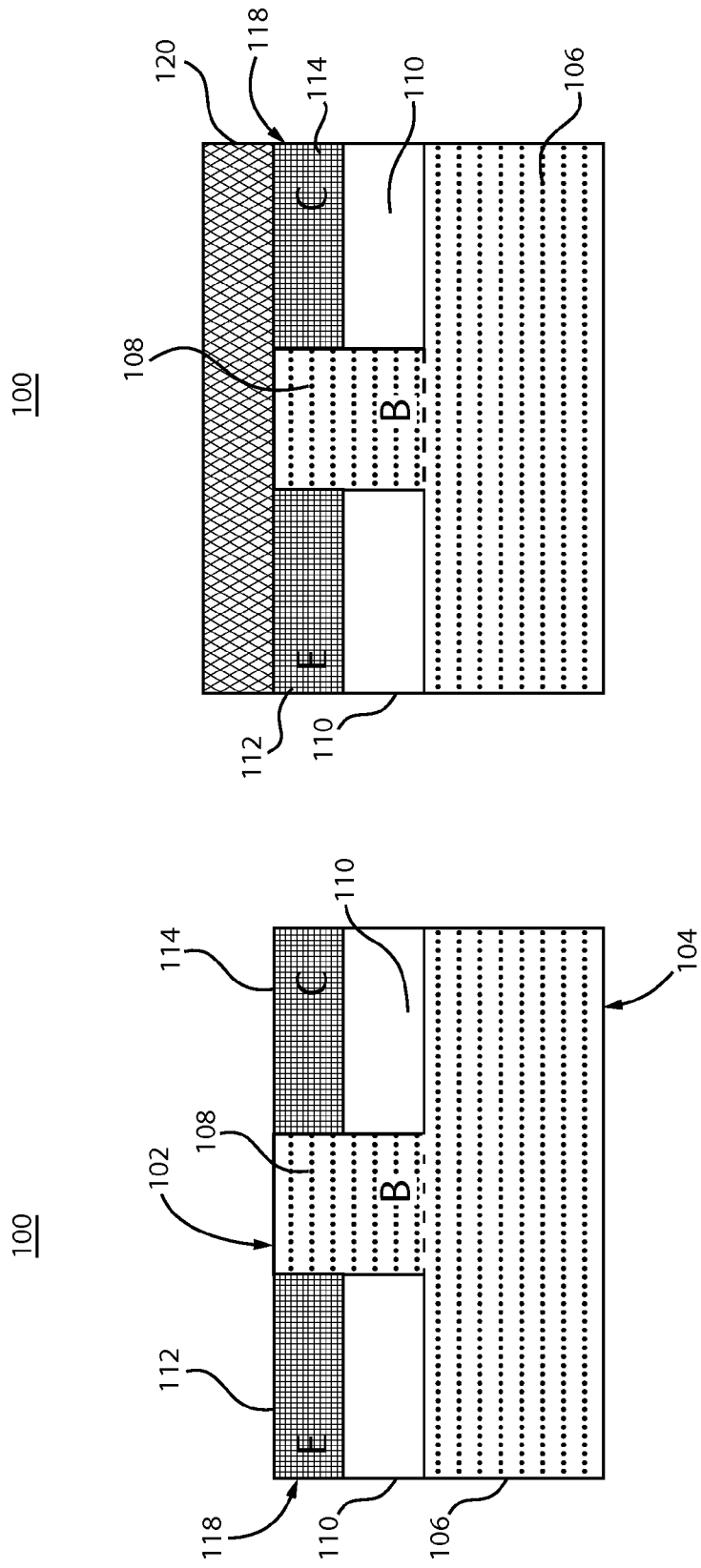

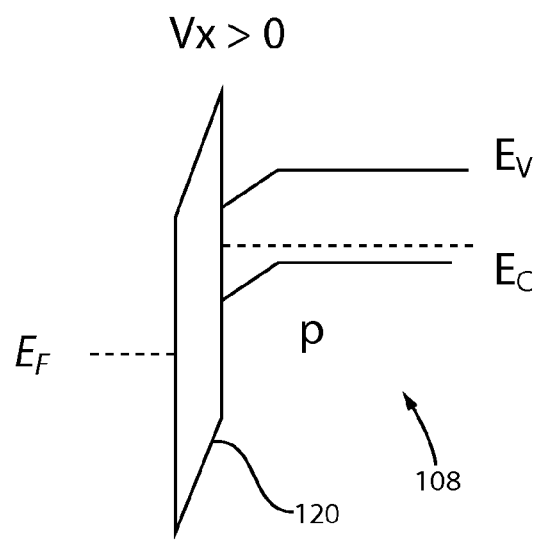
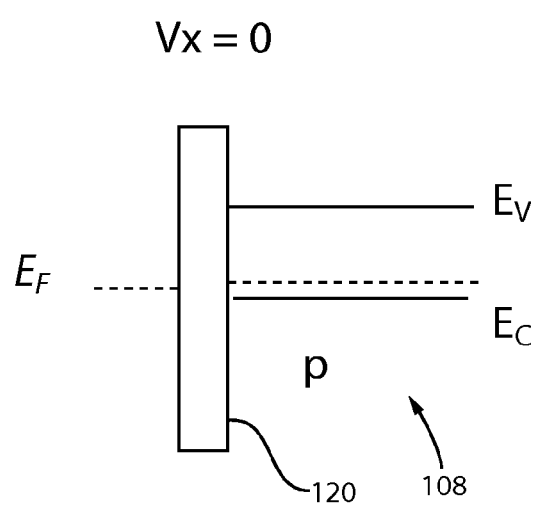
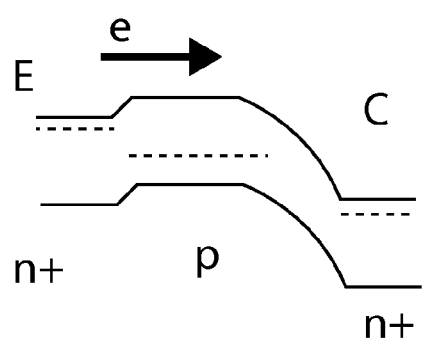
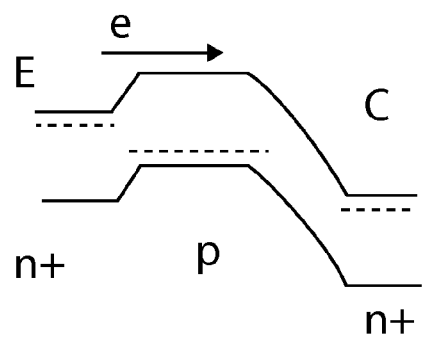
FIG. 3
FIG. 4

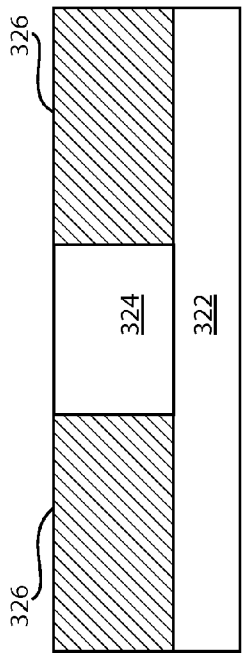
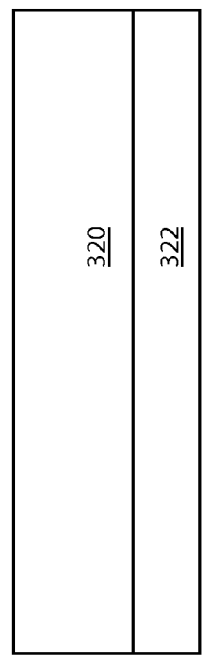
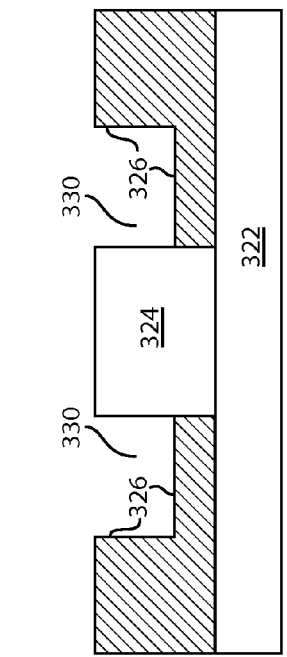
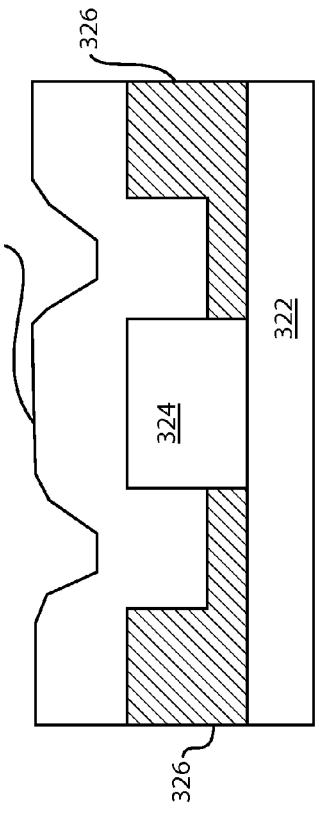
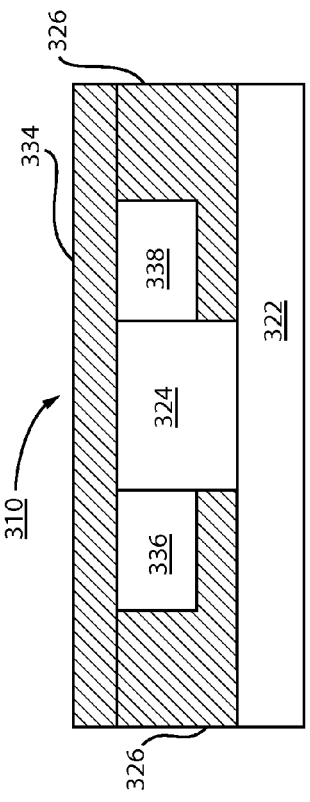
FIG. 10A
FIG. 10B
FIG. 10C
FIG. 10D
FIG. 10E

CHARGE SENSORS USING INVERTED LATERAL BIPOLAR JUNCTION TRANSISTORS

BACKGROUND

1. Technical Field

The present invention relates to semiconductor devices, and more particularly to charge sensors formed using inverted lateral bipolar junction transistors.

2. Description of the Related Art

Conventionally, different types of sensors are fabricated for the detection of different materials/substances. For example, Geiger counters are used to detect the radiation dose and provide a real-time but semi-quantitative readout. Personal radiation dosimeters in the form of wearable badges are available but cannot provide real time readout. Bio-sensors, depending on the materials to detect, include quite different structures, which very often require a certain amount of time for readout due to the reaction/detection mechanism. Moreover, better resolution/sensitivity requires longer processing time, which sometimes involves special instruments only available in laboratories, limiting the portability of bio-sensors.

SUMMARY

A sensor includes a collector, an emitter and a base-region barrier formed as an inverted bipolar junction transistor having a base substrate forming a base electrode to activate the inverted bipolar junction transistor. A level surface is formed by the collector, the emitter and the base-region barrier opposite the base substrate such that when the level surface is exposed to charge, the charge is measured during operation of the bipolar junction transistor.

Another sensor includes a collector, an emitter and a base-region barrier formed as an inverted bipolar junction transistor having a base substrate forming a base electrode to activate the inverted bipolar junction transistor. A level surface is formed by the collector, the emitter and the base-region barrier opposite the base substrate such that when the level surface is exposed to charge, the charge is measured during operation of the bipolar junction transistor. A detection layer is disposed over the level surface and configured to interface with an item to be measured such that interaction or contact with the substance generates charge measurable by the bipolar junction transistor.

Yet another sensor includes a base substrate including a monocrystalline semiconductor material, a base-region barrier extending from the base substrate and including a monocrystalline structure having a same dopant conductivity as the base substrate, an emitter contacting a first lateral side of the base-region barrier, and a collector contacting a second lateral side opposite the emitter to form a bipolar junction transistor. The emitter and collector are spaced from the base substrate by a buried dielectric layer. The collector, the emitter and the base-region barrier form a level surface opposite the base substrate. A detection layer is disposed over the level surface such that when the detection layer is exposed to charge, the charge is measured during operation of the bipolar junction transistor.

A method for forming a sensor includes forming a base-region barrier in contact with a base substrate, the base-region barrier including a monocrystalline semiconductor having a same dopant conductivity as the base substrate; forming an emitter and a collector in contact with and on opposite sides of the base-region barrier to form a bipolar junction transistor; and planarizing the collector, the emitter and the base-region barrier to form a level surface opposite the base substrate such that when the level surface is exposed to charge, the charge is measured during operation of the bipolar junction transistor.

Another method for forming a sensor includes providing a semiconductor on insulator (SOI) substrate having a base substrate, a buried dielectric layer on the base substrate and a first semiconductor layer on the buried dielectric layer; patterning the first semiconductor layer to shape an emitter and a collector; etching through the buried dielectric layer to expose a portion of the base substrate; epitaxially growing a base-region barrier extending from the portion of the base substrate to a position between the emitter and the collector, the base-region barrier being in contact with the emitter and the collector to form a bipolar junction transistor, the base-region barrier including a same dopant conductivity as the base substrate; planarizing the collector, the emitter and the base-region barrier to form a level surface opposite the base substrate such that when the level surface is exposed to charge, the charge is measured during operation of the bipolar junction transistor; and forming a detection layer on the level surface.

A sensing method includes providing a sensor having a collector, an emitter and a base-region barrier formed as an inverted bipolar junction transistor having a base substrate forming a base electrode to activate the inverted bipolar junction transistor, and a level surface formed by the collector, the emitter and the base-region barrier opposite the base substrate such that when the level surface is exposed to charge, the charge is measured during operation of the bipolar junction transistor; accumulating charge at or near the level surface; and activating the base substrate as a base electrode to enable the bipolar junction transistor to measure a dose or number of interactions which is proportional to the accumulated charge.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein:

FIG. 1 is a cross-sectional view of a sensor device including an inverted lateral bipolar junction transistor (ILBJT) in accordance with the present principles;

FIG. 2 is a cross-sectional view of the sensor device including a detection layer on the ILBJT in accordance with the present principles;

FIG. 3 is a band diagram showing bands of the sensor of FIG. 1 when charge (non-zero voltage) is applied to a top surface in accordance with the present principles;

FIG. 4 is a band diagram showing bands of the sensor of FIG. 1 when no charge (a zero voltage) is applied to a top surface in accordance with the present principles;

FIGS. 10A-10E show cross-sectional views of a method for forming a sensor in accordance with one illustrative embodiment;

DETAILED DESCRIPTION OF PREFERRED EMBODIMENTS

Figure 6:
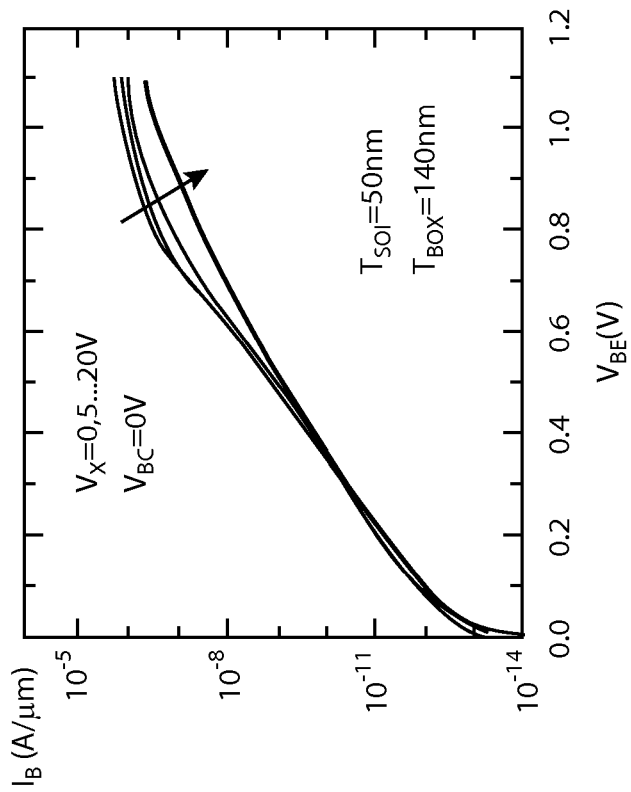
FIG. 6 shows barrier current ($I_B$) in A/micron versus base-emitter voltage ($V_{BE}$) in volts for different applied voltages (Vx) for measuring accumulated charge in accordance with the present principles.

The present principles provide a smart charge sensor fabricated with an inverted lateral semiconductor-on-insulator (SOI) Bipolar Junction Transistor (BJT). The smart charge sensor may function as a radiation dosimeter, a bio-sensor, or any other detection device with proper engineering of detection layers that can be independently placed on top of the sensor. The sensor exhibits high sensitivity and long-term charge retention to enable long-term tracking. The smart sensor can be enabled for detection of radiation, biological entities and chemical entities with appropriate structure/material engineering. The structure of the smart sensor is preferably a Si-based device built on the inverted lateral SOI bipolar junction transistor (BJT) and its detection mechanism is charge detection, which can be provide measurements in real-time by measuring the charge.

In comparison to both fully-depleted silicon-on-insulator (FDSOI) metal oxide semiconductor filed effect transistors (MOSFET) and its bulk counterparts, the inverted lateral SOI BJT charge sensor, in accordance with the present principles, has at least the following advantages. The sensor has ideal 60 mV/decade of $I_C$-$V_{BE}$ (collector current-base-emitter voltage) characteristics, versus >60 mV/decade of $I_D$-Vgs (drain current-gate-source voltage) characteristics of other technologies. The present sensors are not limited by the thickness of a buried oxide layer (BOX) or SOI substrate. FDSOI MOSFETs require a thin SOI substrate (e.g., less than 40 nm), which needs to be fully depleted in use, implying a potential contact resistance penalty. Also, the sub-threshold slope of the $I_D$-Vgs characteristics for the MOSFET is usually >60 mV/decade. These sub-threshold characteristics (threshold voltage, Vt) may deviate from the linear dependence of radiation dose especially at extremely high dose. A sensing layer for the present sensor can be readily custom engineered for a particular application. Good charge retention is rendered by using a dielectric, e.g., silicon dioxide, as a sensing layer for the present sensors.

It is to be understood that the present invention will be described in terms of a given illustrative device architecture having an inverted lateral SOI or SOI-like BJT design; however, other architectures, structures, substrate materials and process features and steps may be varied within the scope of the present invention.

It will also be understood that when an element such as a layer, region or substrate is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

A design for an integrated circuit chip in accordance with the present principles may be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer may transmit the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

Methods as described herein may be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

Sensors in accordance with the present principles may be embedded in cell phones, music players, satellite positioning devices, or even built into credit cards, driver's licenses, etc. In one application, a present sensor may be employed by first responders to provide a reading device that would download integrated doses of materials so that treatment decisions could be made quickly. Other applications are also contemplated.

Referring now to the drawings in which like numerals represent the same or similar elements and initially to FIG. 1, a charge sensor 100 (e.g., an inverted lateral bipolar junction transistor (ILBJT)) is shown in accordance with one embodiment. In this embodiment, the charge sensor 100 does not include a detection layer over a top surface 102. The charge sensor 100 may be formed using a semiconductor-on-insulator (SOI) substrate 104, although other substrates and bulk materials may be employed to form the same structure. The sensor 100 includes a base substrate 106 having a monocrystalline structure. The base substrate 106 may include silicon, germanium, SiGe, GaAs, or any other semiconductor material. The base substrate 106 functions as a base electrode (hence inverted since the base electrode is on the bottom of the device). The base substrate 106 is coupled to a separately formed (grown) base-region barrier 108 which is the intrinsic base (or simply called the base) of the ILBJT. Base-region barrier 108 is preferably grown from the base substrate 106 and includes a monocrystalline or crystalline structure having the same materials as the base substrate 106.

A buried dielectric layer 110 separates the base substrate 106 from an emitter 112 and a collector 114. The buried dielectric layer 110 may include oxide (e.g., silicon dioxide) although other dielectric materials are contemplated. The emitter 112 and collector 114 may be formed (patterned and doped) from a thin semiconductor layer 118 (e.g., from the SOI structure). The emitter 112 and collector 114 may include silicon, germanium, SiGe, GaAs, etc. The sensor 100 may include different conductivities and dopant types. In one embodiment, the emitter 112 and collector 114 are n+ doped while the base substrate 106 and the base-region barrier 108 are p doped. This forms an NPN bipolar junction transistor. In other embodiments, a PNP bipolar junction transistor may be employed.

The operation of the sensor 100 provides current injected from the n+ emitter 112 (E), across the base-region barrier (B) 108 to reach the n+ collector (C) 114. This charge flows upon activation of the base substrate 106. Activation of the base substrate 106 may include applying a voltage to the entire base substrate 106 or the base substrate may be isolated into sections and respective sections may be activated by dedicated circuits or connections (not shown). The activation voltage is a threshold voltage that permits charge to flow across the base-region barrier 108 from emitter 112 to collector 114. While the sensor 100 may be employed in this form, preferred embodiments include a detection layer interface and/or an accumulation layer.

The emitter 112, collector 114 and base-region barrier 108 form a level surface 102. The surface 102 is preferably planar so that charge will evenly be distributed over the surface 102. In other designs, different surface shapes may be employed to provide different functionality, and cause charge build-up/accumulation at pre-determined locations on the surface of the sensor 100.

Referring to FIG. 2, a detection layer 120 is formed over a surface of the emitter 112, base-region barrier 108 and collector 114. The detection layer 120 is configured to interact with, react with or otherwise interface with radiation, chemicals, mechanical elements, bio-matter, etc. The detection layer 120 is configured to cause the generation of charge that affects operation of the sensor 100 so that a measurement of charge can be made.

In the embodiment of FIG. 1, no detection layer 120 is employed. This permits the measurement of induced charge or other charge that comes in contact with a top surface of the sensor 100 (e.g., an aqueous solution of ions, etc.). In the embodiment of FIG. 2, the detection layer 120 acts as an interface with the material or materials that are to be measured. In some embodiments, the detection layer 120 generates or accumulates measurable charge as a result of its interaction with the item or material(s) to be measured. During operation, charge present at or near a top layer of the sensor 100 causes depletion in the base-region barrier 108 at or near the surface 102. A reading of this accumulated charge can be performed by activating the sensor 100 by enabling the base electrode (base substrate 106) to permit the sensor 100 to operate (cause current flow).

Referring to FIG. 3, a band diagram is illustratively shown for the sensor 100. The band diagram shows the valence band edge $E_v$ and the conduction band edge $E_c$ versus a spatial dimension. A Fermi level ($E_F$) is indicated in the diagram. If there is positive charge (either through trapping or surface functionalization) in the detection layer 120 (or at/through the top surface of the sensor 100), the lateral BJT responds as if a positive voltage (Vx>0) is applied to the top of the inverted lateral SOI BJT (sensor 100) (e.g., a NPN device in this case). This causes depletion in the base-region barrier 108 near the surface (102). The barrier is lowered due to the depletion, leading to an increase in collector current ($I_C$).

Referring to FIG. 4, another band diagram is illustratively shown for the sensor 100 when (Vx=0). If there is no net charge in the detection layer 120 (or through the top surface of the sensor 100), the lateral BJT responds as if no voltage is applied to the top of the inverted lateral SOI BJT (sensor 100) (e.g., a NPN device in this case). The ILBJT operates normally without any change in collector current.

Figure 5:
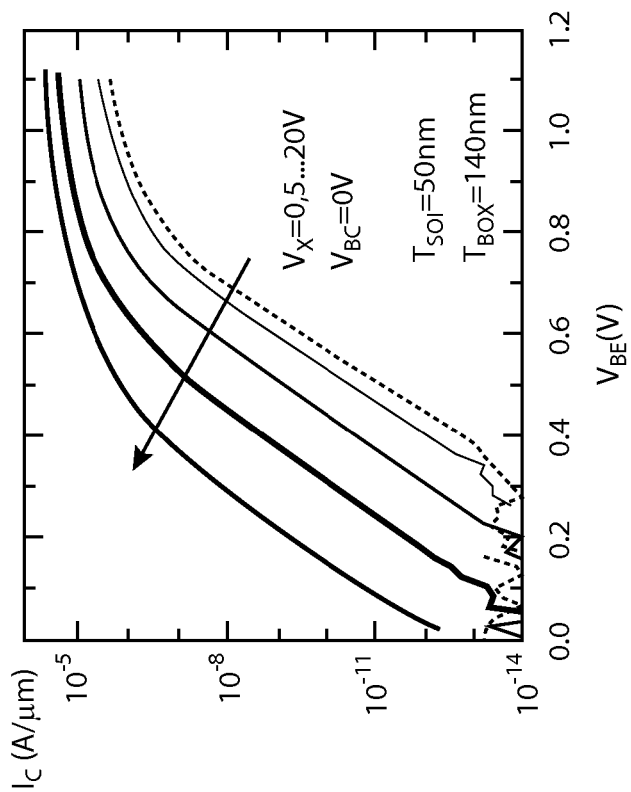
FIG. 5 shows collector current ($I_C$) in A/micron versus base-emitter voltage ($V_{BE}$) in volts for different applied voltages (Vx) for measuring accumulated charge in accordance with the present principles.

Referring to FIG. 5, plots showing collector current ($I_C$) (in A/micron) at base-emitter voltage ($V_{BE}$) of 0.4V for varying Vx (Vx=0, 5, . . . , 20V) are illustratively depicted. The plots are generated using a buried oxide layer 140 nm in thickness and a silicon layer thickness for the collector and emitter of 50 nm. Also, the voltage from base to collector ($V_{BC}$) was zero.

Referring to FIG. 6, plots showing base current ($I_B$) (in A/micron) versus base-emitter voltage ($V_{BE}$) (in volts) for varying Vx (Vx=0, 5, . . . , 20V) are illustratively depicted. The plots are generated using the buried oxide layer 140 nm in thickness and a silicon layer thickness for the collector and emitter of 50 nm. Also, the voltage from base to collector ($V_{BC}$) was zero.

Data of $I_C$ and $I_B$ shown in FIGS. 5 and 6 depicts modulation (increased Vx), which simulates accumulated charge in the detection layer 120. Note that the modulation of $I_C$ and $I_B$ due to the charge is similar in shape in both FIGS. 5 and 6.

Figure 7:
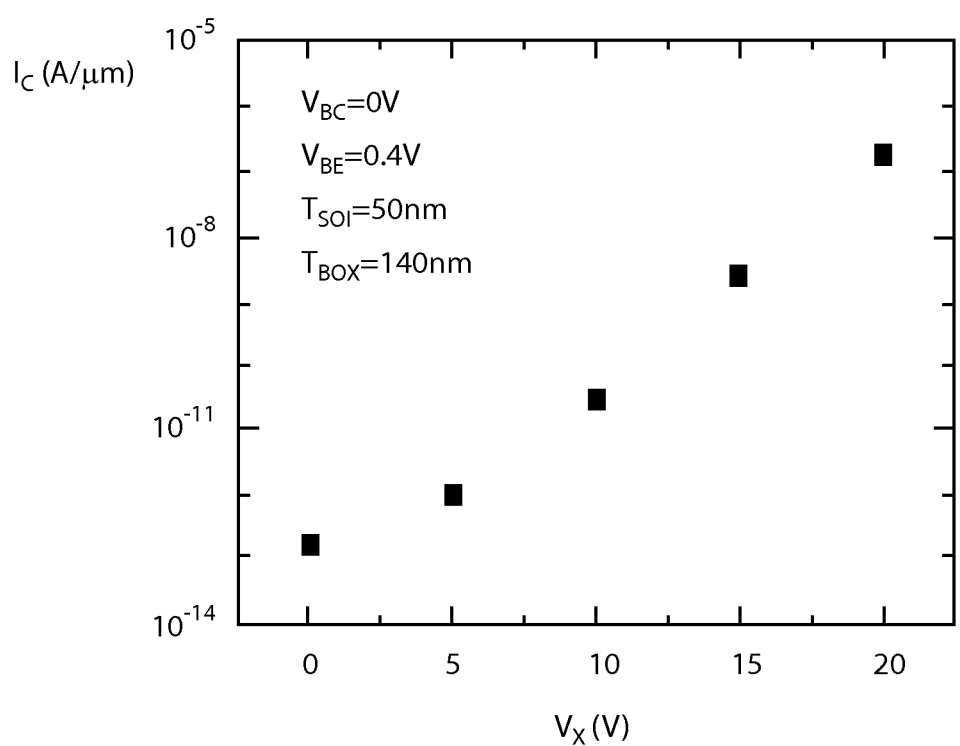
FIG. 7 shows collector current ($I_C$) in A/micron versus applied voltage (Vx) in volts for $V_{BE}$=0.4V for measuring accumulated charge (dose, radiation, etc.) in accordance with the present principles.

Referring to FIG. 7, data point plots showing collector current ($I_C$) (in A/micron) versus Vx (in volts), varying as 0, 5, . . . , 20V, are illustratively depicted. The plots are generated using a buried oxide layer 140 nm in thickness and a silicon layer thickness for the collector and emitter of 50 nm. Also, the voltage from base to collector ($V_{BC}$) was zero, and $V_{BE}$ was 0.4V. The change of $I_C$ as a function of Vx (from oxide charge) at $V_{BE}$=0.4V is plotted and shows an exponential increase in $I_C$ with Vx. This exponential dependence of $I_C$ on Vx makes the sensor 100 (e.g., an inverted lateral SOI BJT) more suitable than MOSFETs, which provide a linear change of threshold voltage with oxide charge for charge detection. The present embodiments provide the advantage of the 60 mV/decade $I_C$-$V_{BE}$ characteristics as opposed to >60 mV/decade for $I_d$-$V_{gs}$ using a MOSFET. Such advantages permit increased sensitivity and provide more reliable readings without the physical limitations of fully depleted MOSFETs (e.g., limitations of silicon thickness, etc.).

Figure 8:
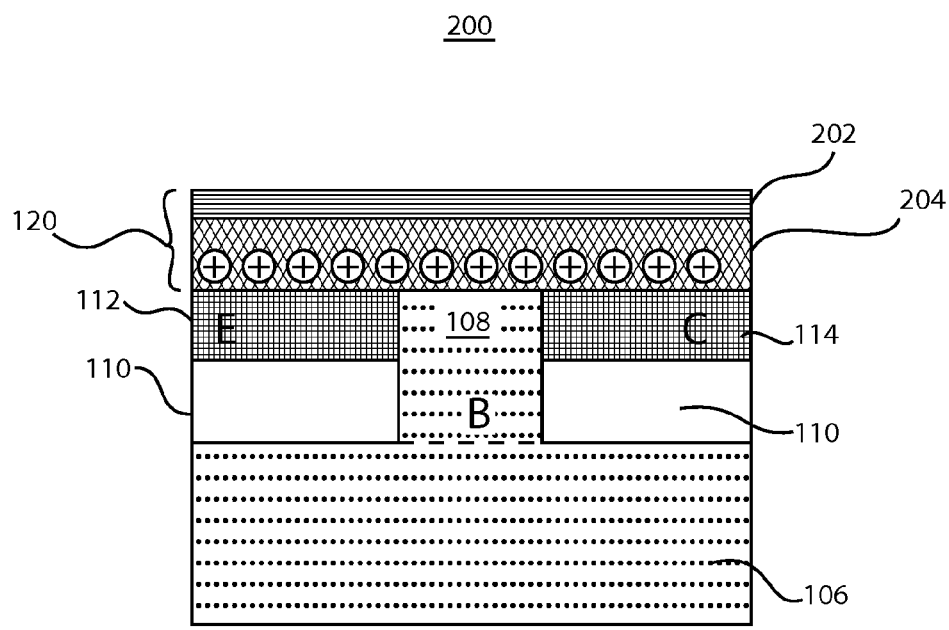
FIG. 8 is a cross-sectional view of a sensor device including a detection layer having a conversion layer and an accumulation layer for measuring radiation (thermal neutrons) in accordance with the present principles.

Referring to FIG. 8, one embodiment of the sensor 100 includes a radiation dosimeter 200. The dosimeter 200 includes a detection layer 120 that can be configured as an interface to provide charge to be sensed. The dosimeter 200 may be adapted to make measurements of charged or other emitted particles. Since the effect of Vx>0 is equivalent to positive charge in the detection layer 120, ionizing radiation creates a similar modulation of $I_C$ as described above. Therefore, the inverted lateral SOI BJT can be utilized as the radiation dosimeter 200 by measuring the change in its $I_C$ as a function of radiation dose.

In the embodiment of FIG. 8, the dosimeter 200 includes an inverted lateral SOI BJT, which functions to measure thermal neutrons (n). Thermal neutrons are neutrons having energy capable of causing a nuclear fission reaction. Detection of these neutrons can be useful for detecting nuclear events (e.g., the event of nuclear plant meltdown or radiological-dispersal bomb detonation) or for monitoring operations or safety in nuclear facilities.

A thermal neutron conversion layer 202 is incorporated into the detection layer 120. The conversion layer 202 is preferably formed over a charge accumulation layer 204, which is preferably a dielectric layer or stack of layers. In one embodiment, the charge accumulation layer 204 includes an oxide layer (e.g., $SiO_2$) although other dielectric materials may also be employed, e.g., silicon nitride, etc. Incoming thermal neutrons will react with the material of the conversion layer 202 and generate ionizing particles, e.g., alpha particles ($\alpha$) ($He^{2+}$), protons (p), X-rays ($e^-$), gamma ($\gamma$) rays, beta particles ($\beta$), etc. which create positive charge 206 that is eventually trapped in the accumulation layer 204.

The thermal neutron conversion layer 202 may be comprised of a single material, multiple materials or layers of materials. The materials are configured and dimensioned (e.g., thicknesses) to cause an appropriate reaction for generating charge to be accumulated in the accumulation layer 204. TABLE 1 shows some illustrative materials, the reactions of the materials with thermal neutrons and some of the materials' characteristics. The materials that may be employed in the thermal neutron conversion layer 202 have an isotopic abundance for the isotope of the material which is listed in TABLE 1. The particles emitted by the reaction and the respective energy of the reaction are also shown. The reactions shown in TABLE 1 all have large cross sections for thermal neutron capture but the outgoing particles are emitted at relatively low energy. The range of these ions in silicon (e.g., penetration depth) as a function of their energy results in most of the outgoing charged particles being absorbed in a few micrometers in silicon.

These outgoing charged particles would stop completely if directed onto the thick silicon substrate below the sensor device (base substrate). Notwithstanding this, additional shielding or moderating materials may be employed to ensure the outgoing charged particles are completely contained. The additional shielding or moderating materials may be configured to support omnidirectional thermal neutron measurements. The dosimeter would detect thermal neutrons in any orientation, since the thermal neutrons would easily penetrate the top or sides of the dosimeter.

TABLE 1

| Reaction | Isotopic abundance (%) | Emitted particle and energy | Emitted particle and energy | Cross Section (B) |
|---|---|---|---|---|
| $^{10}B$ (n, $\alpha$) | 19.8 | $^7Li$, 0.84 MeV | $\alpha$, 1.47 MeV | 3840 |
| $^6Li$ (n, $\alpha$) | 7.4 | $^3H$, 2.73 MeV | $\alpha$, 2.05 MeV | 940 |
| $^3He$ (n, p) | 1.4E-4 | $^3H$, 0.19 MeV | p, 0.57 MeV | 5330 |
| $^{157}Gd$ (n, $e^-$) | 15.7 | $e^-$, 72 keV | | 255,000 |

Figure 9:
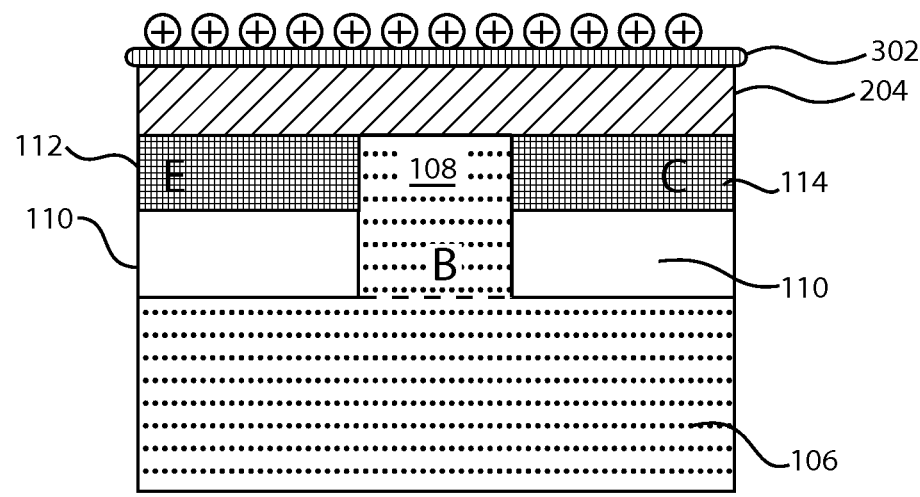
FIG. 9 is a cross-sectional view of a sensor device including a detection layer having a surface layer and an accumulation layer for measuring chemical bonds (bio-materials or inorganic materials) in accordance with the present principles.

Referring to FIG. 9, another embodiment of the sensor 100 includes a bio-sensor 300. The bio-sensor 300 includes a detection layer 120 that can be configured as an interface to provide charge to be sensed from contact or interaction with bio-materials. The bio-sensor 300 includes the inverted lateral SOI BJT structure as described above with a detection surface 302 for sensing of bio-molecules, such as proteins, viruses, ions, etc. from solution or in air. As before, $I_C$ would be monitored as the sensing signal at a fixed $V_{BE}$.

The surface 302 may be distributed over an accumulation layer 204. The surface 302 would include or be modified so as to specifically bind a molecule or compound under study. For example, to detect a specific protein (such as, e.g., streptavidin), the surface 302 would be coated with a corresponding antibody (such as, e.g., biotin) that specifically binds the proteins of interest. Since most bio-molecules are charged, bound bio-molecules would create charge on the surface 302 with a concomitant change in the voltage Vx. This bio-molecule induced change in Vx would cause the sensing signal $I_C$ to exponentially vary as shown in FIG. 5. Hence, the bio-sensor 300 detects bio-molecules with high sensitivity at low sensing voltages $V_{BE}$.

Referring to FIGS. 10A-10E, a method for forming a sensor 310 is shown in accordance with one illustrative embodiment. In FIG. 10A, a semiconductor material 320 is formed on or grown on a substrate 322. In one embodiment, the semiconductor layer 320 is p doped and the substrate is p+ doped. In other embodiments, the semiconductor layer 320 is n doped and the substrate is n+ doped. The semiconductor layer 320 and substrate 322 may include monocrystalline silicon or other materials described for base-region barrier 108 and base substrate 106, respectively.

In FIG. 10B, the semiconductor layer 320 is patterned and etched or otherwise shaped, as needed, for a base-region barrier 324. A dielectric layer is deposited and planarized to the base-region barrier 324 to form dielectric trench regions 326. The dielectric trench regions 326 may include an oxide or other suitable material.

In FIG. 10C, the dielectric trench regions 326 are masked and etched (e.g., reactive ion etching) to form trenches 330. The trenches 330 define regions for the formation of emitter and collector regions. In FIG. 10D, a doped polysilicon layer 332 is deposited in the trenches. In this example, the polysilicon is n+ doped; however, if the base region 324 and the substrate 322 are n-doped, the polysilicon is p+ doped.

In FIG. 10E, the polysilicon 332 is planarized to form a level surface (from the barrier 324, an emitter 336 and a collector 338) for the ILBJT device 310. A detection layer 334 may be deposited over the base region barrier 324, the emitter 336 and the collector 338. Additional steps include forming contacts and other metallizations to provide connections to the appropriate regions of the ILBJT 310.

Figure 11:
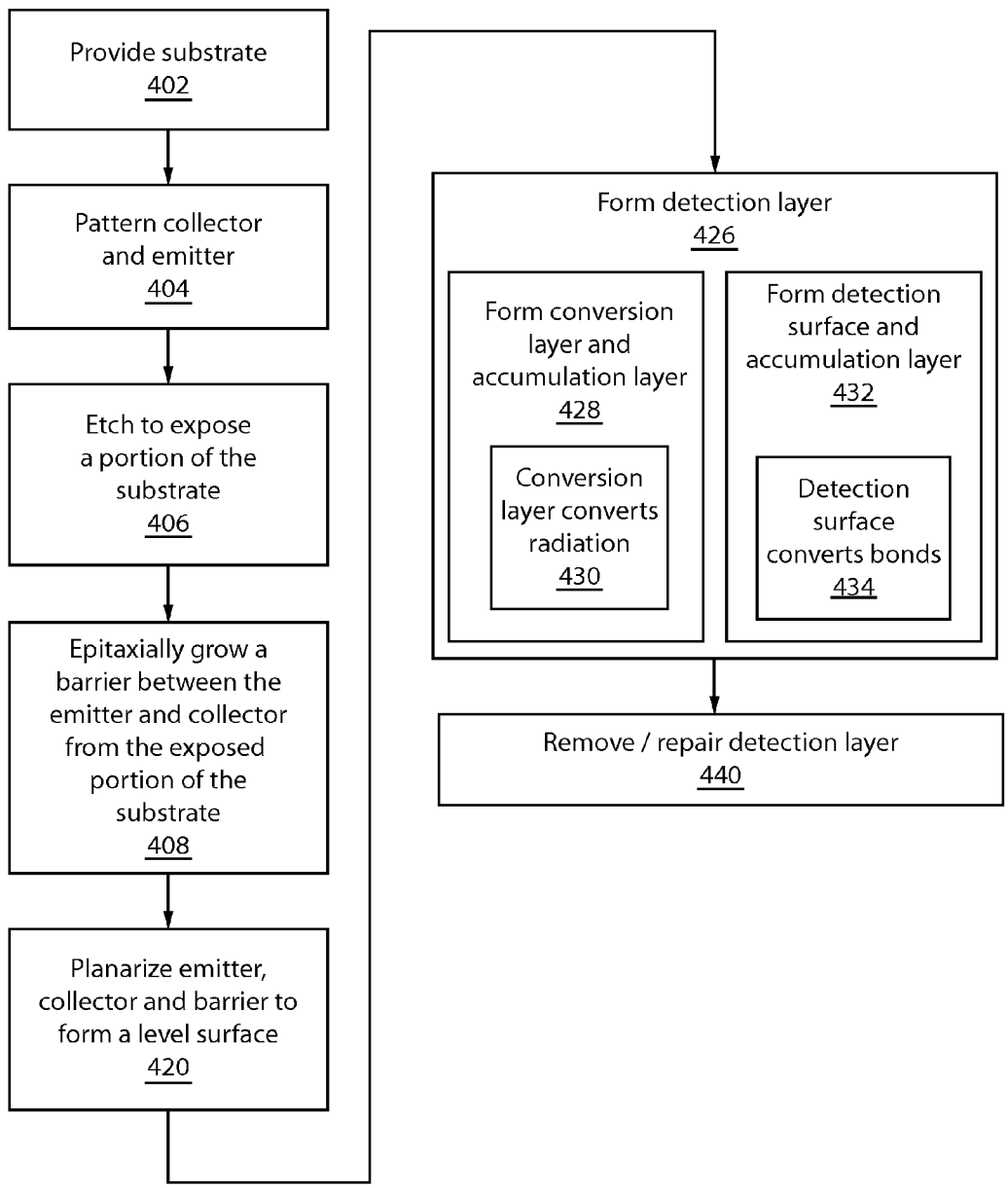
FIG. 11 is a block/flow diagram showing other methods for fabricating a sensor in accordance with illustrative embodiments.
Figure 12:
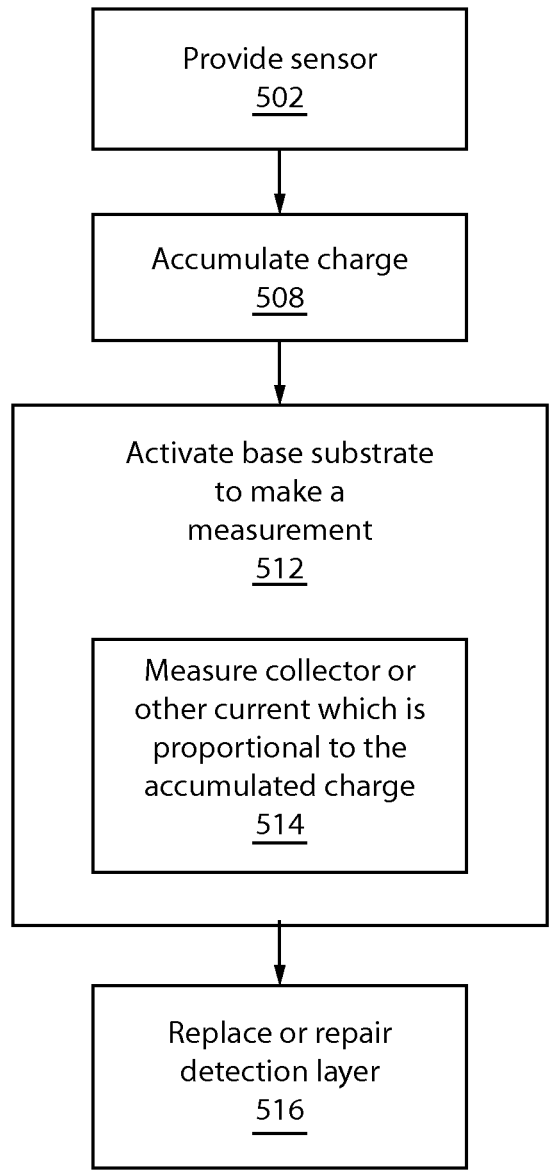
FIG. 12 is a block/flow diagram showing a method for employing a sensor in accordance with illustrative embodiments.

Referring to FIGS. 11 and 12, aspects of the present invention are described below with reference to flowchart illustrations and/or block diagrams of methods according to embodiments of the invention. The flowchart and block diagrams in the FIGs. illustrate the architecture, functionality, and operation of possible implementations according to various embodiments of the present invention. It should also be noted that, in some alternative implementations, the functions noted in the blocks may occur out of the order noted in the FIGs. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Referring to FIG. 11, another method for forming a sensor is illustratively shown in accordance with exemplary embodiments. In block 402, a substrate is provided. The substrate may include a semiconductor on insulator (SOI) substrate having a base substrate, a buried dielectric layer on the base substrate and a first or top semiconductor layer on the buried dielectric layer. Other substrates and materials may also be employed to provide the structure described herein in accordance with the present principles (FIG. 10A). In block 404, the first semiconductor layer is patterned to shape an emitter and a collector. The patterning may include etching the emitter and collector shapes in the first semiconductor layer as well as etching through a portion of the buried dielectric layer. In block 406, the buried dielectric layer is etched to expose a portion of the base substrate. The etching may remove a small portion of the base substrate as well to expose a pristine area to grow a base-region barrier structure. Note that the base substrate or portions thereof are connected to circuits, contacts, etc. to permit a voltage to be applied thereto to activate a resultant BJT device as will be described.

In block 408, a base-region barrier is epitaxially grown extending from the portion of the base substrate to a position between the emitter and the collector. The base-region barrier is in contact with the emitter and the collector on opposite lateral sides to form a bipolar junction transistor. The barrier includes a same dopant conductivity as the base substrate. The barrier may be doped in-situ or after formation using known doping methods. The base substrate may be doped in advance as well by known methods.

In block 420, the collector, the emitter and the base-region barrier are planarized to form a level surface on top (e.g., opposite the base substrate) such that when the level surface is exposed to charge, the charge is measured during operation of the bipolar junction transistor. Planarization may include chemical mechanical polishing (CMP) or other processes.

In block 426, a detection layer may be formed on the level surface. In block 428, the detection layer may be formed from an accumulation layer and a conversion layer such that the conversion layer turns interactions with the conversion layer into charge which is accumulated in the accumulation layer. In block 430, the conversion layer may be configured to convert incident radiation into charge; the radiation may include at least one of alpha particles, beta particles, protons, neutrons, electromagnetic radiation, etc.

In block 432, the detection layer may be formed from an accumulation layer and a detection surface such that the detection surface is configured to bond with a material to provide charge which is accumulated in the accumulation layer. In block 434, the detection surface may be configured to convert molecular bonds into charge. The molecular bonds include at least one of bonds with proteins, viruses and ions. The bonds may also include chemical bonds for inorganic compounds, other bio-materials and elements.

In block 440, the detection layer may be removed, e.g., by etching or other processing, and the detection layer may be restored, renewed or repaired as needed. In addition the detection layer may be reconfigured to permit sensing operations of different materials using the same base device (ILBJT). In other embodiments, a plurality of sensors may be employed in an array to sense a same radiation, compound etc. or different radiations, compounds, etc.

Referring to FIG. 12, a sensing method using the sensors in accordance with the present principles is illustratively shown in accordance with exemplary embodiments. In block 502, a sensor is provided having a collector, an emitter and a base-region barrier formed as an inverted bipolar junction transistor and having a base substrate that forms a base electrode to activate the inverted bipolar junction transistor. A level surface is formed by the collector, the emitter and the base-region barrier opposite the base substrate such that when the level surface is exposed to charge, the charge is measured during operation of the bipolar junction transistor. The sensor preferably includes a detection layer on the level surface.

The detection layer may include an accumulation layer and a conversion layer such that the conversion layer turns interactions with the conversion layer into charge which is accumulated in the accumulation layer. The conversion layer may be configured to convert incident radiation into charge, the radiation including at least one of alpha particles, beta particles, protons, neutrons, electromagnetic radiation, etc. The detection layer may include an accumulation layer and a detection surface such that the detection surface is configured to bond with a material to provide charge which is accumulated in the accumulation layer. The detection surface is configured to convert molecular bonds into charge. The molecular bonds may include at least one of bonds with proteins, viruses and ions. The bonds may also include chemical bonds for inorganic compounds or other bio-materials and elements.

In block 508, charge is accumulated at or near the level surface. In block 512, the base substrate is activated as a base electrode to enable the bipolar junction transistor to measure a dose or number of interactions which is proportional to the accumulated charge.

In block 514, the dose or number of interactions is measured using at least one of a collector current and a base current of the inverted bipolar junction transistor, which is proportional to accumulated charge. In one embodiment, an exponential relationship exists between the at least one of the collector current and the base current and a voltage caused by the accumulated charge. In block 516, the detection layer may be replaced or reconfigured, as needed.

Having described preferred embodiments for charge sensors using inverted lateral bipolar junction transistors (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:
1. A sensor, comprising:
a collector, an emitter and a base-region barrier formed as an inverted bipolar junction transistor having a base substrate forming a base electrode to activate the inverted bipolar junction transistor;
a level surface formed by the collector, the emitter and the base-region barrier opposite the base substrate such that when the level surface is exposed to charge, the charge is measured during operation of the bipolar junction transistor; and a detection layer directly on an entirety of the level surface.

2. The sensor as recited in claim 1, wherein the base electrode is selectively activated to enable the inverted bipolar junction transistor to make a measurement.

3. The sensor as recited in claim 1, wherein accumulated charge at or near the level surface affects a collector current of the inverted bipolar junction transistor.

4. The sensor as recited in claim 3, wherein an exponential relationship exists between the collector current and a voltage caused by the accumulated charge.

5. The sensor as recited in claim 1, wherein an accumulated charge in the detection layer is proportional to a dose or number of interactions with material to be measured at the detection layer.

6. The sensor as recited in claim 5, wherein the detection layer includes an accumulation layer and a conversion layer such that the conversion layer turns interactions therewith into charge which is accumulated in the accumulation layer.

7. The sensor as recited in claim 6, wherein the conversion layer converts incident radiation into charge, the radiation including at least one of alpha particles, beta particles, protons, neutrons, and electromagnetic radiation.

8. A sensor, comprising:

a collector, an emitter and a base-region barrier formed as an inverted bipolar junction transistor having a base substrate forming a base electrode to activate the inverted bipolar junction;

a level surface formed by the collector, the emitter and the base-region barrier opposite the base substrate such that when the level surface is exposed to charge, the charge is measured during operation of the bipolar junction transistor; and a detection layer disposed over an entirety of the level surface and configured to interface with an item to be measured such that interaction or contact with the substance generates the charge measurable by the bipolar junction transistor.

9. The sensor as recited in claim 8, wherein the base electrode is selectively activated to enable the inverted bipolar junction transistor to make a measurement.

10. The sensor as recited in claim 8, wherein accumulated charge at or near the level surface affects a collector current of the inverted bipolar junction transistor.

11. The sensor as recited in claim 10, wherein an exponential relationship exists between the collector current and a voltage caused by the accumulated charge.

12. The sensor as recited in claim 8, wherein the detection layer stores an accumulated charge, which is proportional to a dose or number of interactions with the item to be measured.

13. The sensor as recited in claim 8, wherein the detection layer includes an accumulation layer and a conversion layer such that the conversion layer turns interactions therewith into charge which is accumulated in the accumulation layer.

14. The sensor as recited in claim 13, wherein the conversion layer converts incident radiation into charge, the radiation including at least one of alpha particles, beta particles, protons, neutrons, and electromagnetic radiation.

15. A sensor, comprising:

a base substrate including a monocrystalline semiconductor material;

a base-region barrier extending from the base substrate and including a monocrystalline structure having a same dopant conductivity as the base substrate;

an emitter contacting a first lateral side of the base-region barrier; and a collector contacting a second lateral side opposite the emitter to form a bipolar junction transistor, the emitter and collector being spaced from the base substrate by a buried dielectric layer, the collector, the emitter and the base-region barrier forming a level surface opposite the base substrate; and a detection layer disposed over an entirety of the level surface such that when the detection layer is exposed to charge, the charge is measured during operation of the bipolar junction transistor.

16. The sensor as recited in claim 15, wherein the base substrate forms a base electrode to selectively enable operation of the inverted bipolar junction transistor and accumulated charge at or near the level surface affects a collector current of the inverted bipolar junction transistor and further wherein an exponential relationship exists between the collector current and a voltage caused by the accumulated charge.

17. The sensor as recited in claim 15, wherein the detection layer includes an accumulation layer and a conversion layer such that the conversion layer turns interactions therewith into charge which is accumulated in the accumulation layer, wherein the conversion layer converts incident radiation into charge, the radiation including at least one of alpha particles, beta particles, protons, neutrons, and electromagnetic radiation.

* * * * *